United States Patent [19]

Nishioka

[11] Patent Number: 4,678,900
[45] Date of Patent: Jul. 7, 1987

[54] ILLUMINATING OPTICAL SYSTEM FOR ENDOSCOPES

[75] Inventor: Kimihiko Nishioka, Hachiouji, Japan

[73] Assignee: Olympus Optical Co., Ltd., Tokyo, Japan

[21] Appl. No.: 751,240

[22] Filed: Jul. 2, 1985

[30] Foreign Application Priority Data

Jul. 5, 1984 [JP] Japan .................. 59-137983

[51] Int. Cl.$^4$ .................. A61B 1/06; G01J 1/32
[52] U.S. Cl. .................. 250/205; 128/6
[58] Field of Search .................. 250/205, 201 R, 227; 128/6; 354/62; 358/228; 362/276, 277, 285

[56] References Cited

U.S. PATENT DOCUMENTS

| 4,300,167 | 11/1981 | Miller et al. | 358/228 |
| 4,310,228 | 1/1982 | Terada | 354/62 |
| 4,325,618 | 4/1982 | Hosoda | 128/6 |
| 4,443,696 | 4/1984 | Taboada | 250/201 |

FOREIGN PATENT DOCUMENTS 58-87523  5/1983  Japan .

Primary Examiner—Edward P. Westin
Attorney, Agent, or Firm—Cushman, Darby & Cushman

[57] ABSTRACT

An illuminating optical system for endoscopes wherein, in order to make it possible to effect a uniform illumination with a simple structure and without using a mechanical mechanism, a liquid crystal device or electrochromic device is arranged between the entrance end of a light guide and a light source. The transmittance of the light in the part of the liquid crystal device or electrochromic device corresponding to the part brighter than a predetermined value is reduced on the image of an object to be observed. The light guide is formed of many optical fibers or graded index optical fibers arranged to substantially correspond at the entrance end and exit end of the light guide.

14 Claims, 8 Drawing Figures

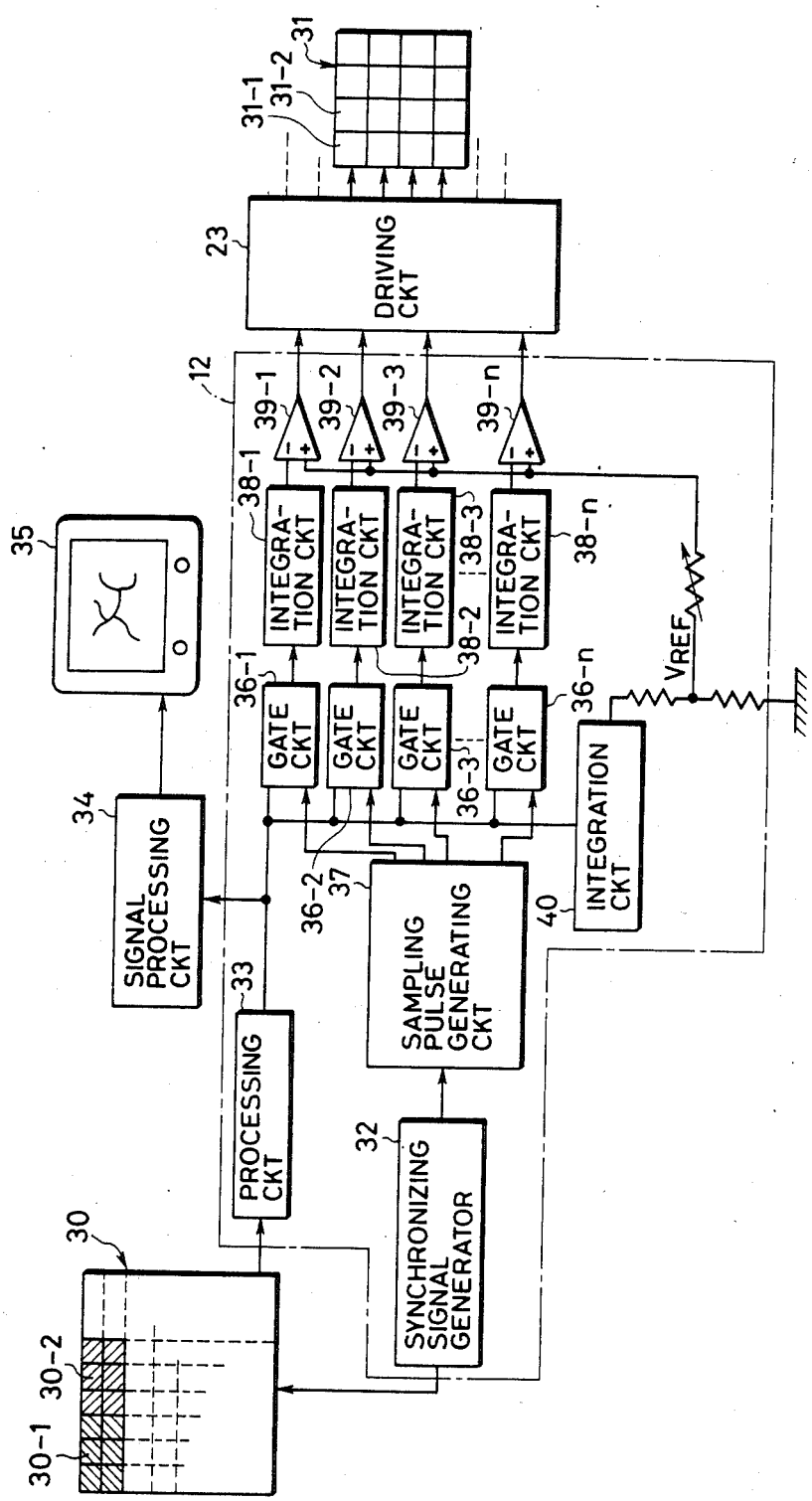

ILLUMINATING OPTICAL SYSTEM FOR ENDOSCOPES

BACKGROUND OF THE INVENTION (a) Field of the Invention:

This invention relates to an illuminating optical system for endoscopes wherein a uniform illumination is obtained with a simple structure.

(b) Description of the Prior Art:

There is already known such illuminating optical systems of this kind as, for example, by Japanese Patent Preliminary Publication No. Sho 58-87523. This shall be explained with reference to FIG. 1. The reference numeral 1 represents an endoscope body including an observing optical system consisting of an objective 2, image guide 3 and eyepiece 4 and an illuminating system consisting of an illuminating lens 5, light guide 6, light collecting lens 7 and light source 8 and further provided with an image receiving device 11 on which an image to be observed is formed by a half prism 9 and lens 10 arranged between the image guide 3 and eyepiece 4, a detecting circuit 12 detecting the brightness distribution in the observing visual field on the basis of a signal from the image receiving device 11 and a driving circuit 13 for moving the light collecting lens 7 in a direction vertical to the optical axis with a signal from the detecting circuit 12. According to this formation, in case the detecting circuit 12 detects an uneven brightness distribution in the observing visual field, the driving circuit 13 will be controlled to drive the light collecting lens 7, and thus the position of the light collecting point by the light collecting lens 7 of the light having come out of the light source 8 will move on the entrance end face of the light guide so that the light distribution characteristic on the object S to be observed will vary and an even uniform illumination will be obtained. However, the illuminating optical system of this type has the disadvantages that a driving mechanism driving the lens to vary the light distribution characteristic is required and that the mechanical structure is complicated.

SUMMARY OF THE INVENTION

In view of the above, a primary object of the present invention is to provide an illuminating optical system for endoscopes wherein an even uniform illumination is obtained with a simple structure.

This object is solved by an illuminating optical system for endoscopes provided with a light guide formed of many fibers and a liquid crystal device or electrochromic device arranged between the entrance end of the light guide and a light source, by which the transmittance can be locally varied in response to the brightness on the image surface.

The above-mentioned object is solved also by an illuminating optical system for endoscopes characterized in that a light guide is formed of graded index optical fibers and a liquid crystal device or electrochromic device by which the transmittance can be locally varied in response to the brightness distribution on the image surface is arranged between the entrance end of the above-mentioned light guide and a light source.

This and other objects of the present invention will become apparent during the course of the following detailed description and appended claims.

BRIEF DESCRIPTION OF THE DRAWINGS

FIG. 8 is a block diagram of a controlling circuit including the detecting circuit and liquid crystal driving circuit shown in the embodiment in FIG. 7.

DESCRIPTION OF THE PREFERRED EMBODIMENTS

Figure 1:
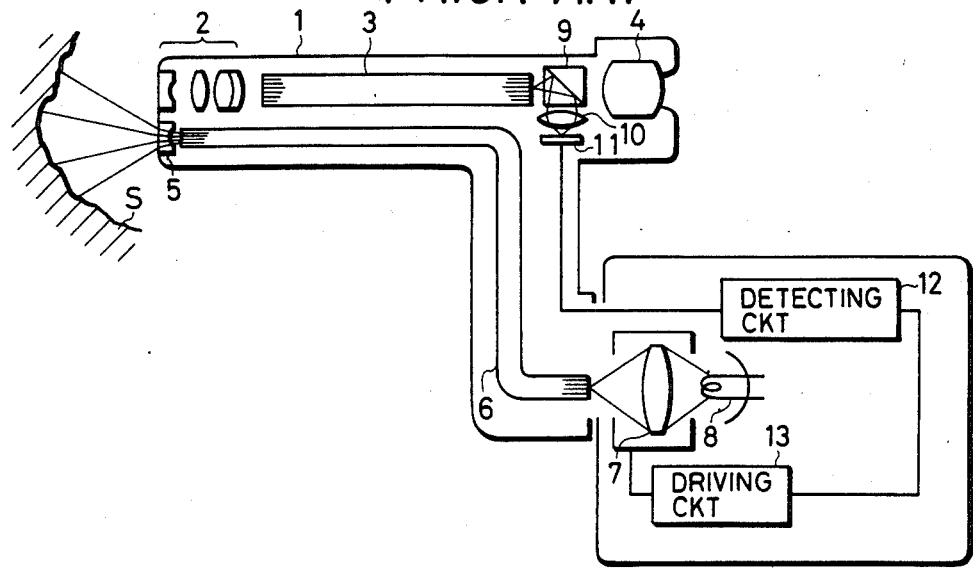
FIG. 1 is a schematic view showing a fundamental formation of a conventional illuminating optical system for endoscopes.
Figure 2:
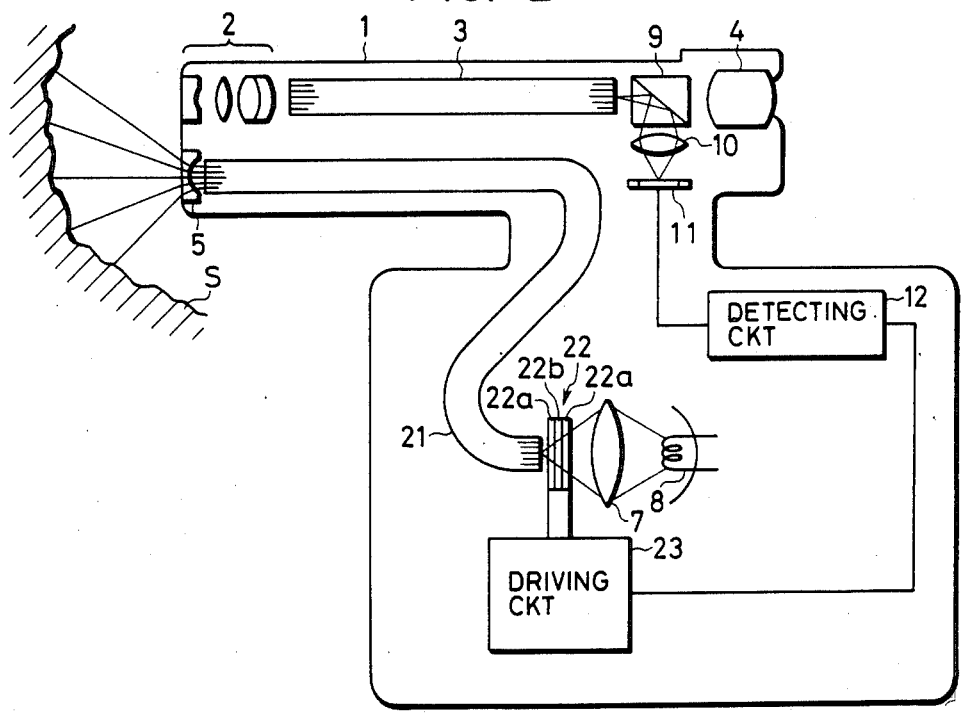
FIG. 2 is a schematic view showing a first embodiment of the illuminating optical system for endoscopes according to the present invention.
Figure 3:
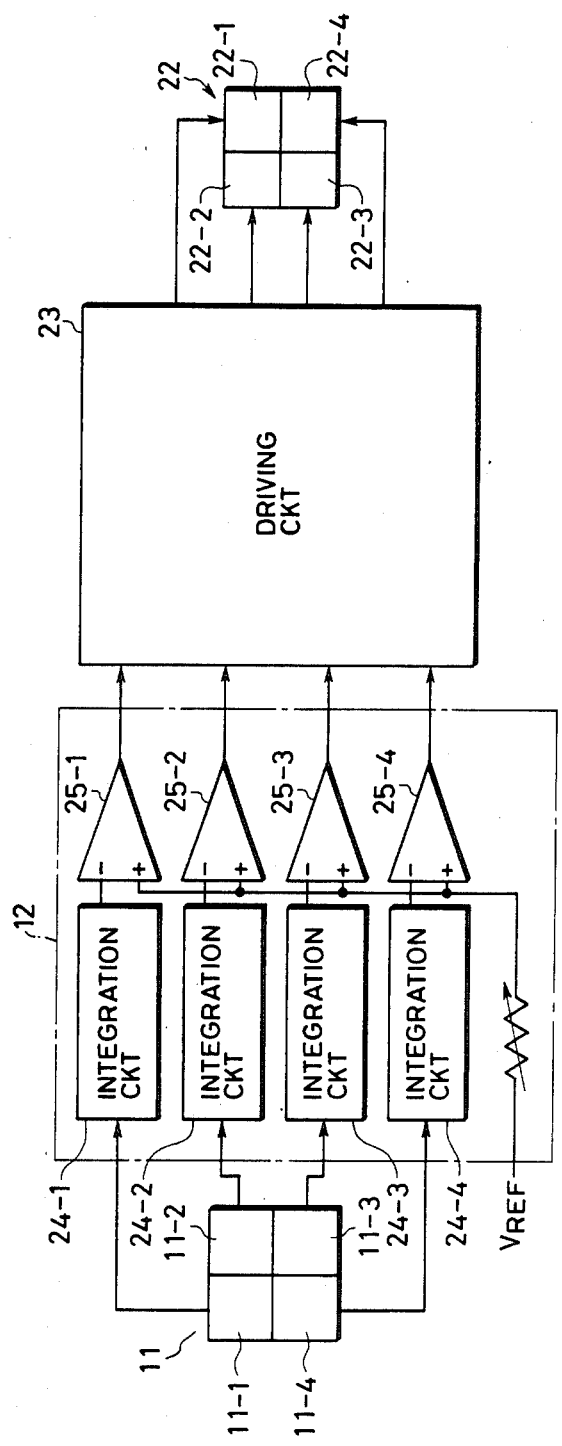
FIG. 3 is a block diagram of a controlling circuit including the detecting circuit and liquid crystal driving circuit shown in the embodiment in FIG. 2.

The present invention shall be explained in the following on the basis of the embodiments shown in the drawings. In FIG. 2, the reference numeral 21 represents a light guide in which respective fibers are located in substantially corresponding positions at the entrance end and exit end, and 22 represents a liquid crystal device arranged near the entrance end of the light guide 21 between the light collecting lens 7 and the entrance end of the light guide 21. Liquid crystal device 22 has a liquid crystal 22b between two electrodes 22a and is divided into a plurality (four in the drawing) of segments as shown in FIG. 3. Each segment may to be independently actuated by a liquid crystal driving circuit 23 which independently actuates the respective segments of the liquid crystal device 22 on the basis of a controlling signal from the detecting circuit 12. The other formations are the same as those of the conventional system shown in FIG. 1; therefore, the same reference numerals are attached to the same respective parts as in FIG. 1.

Now, in FIG. 3, the reference numerals 24-1, 24-2, 24-3 and 24-4 represent integration circuits of detecting circuit 12 connected respectively to elements 11-1, 11-2, 11-3 and 11-4 of the light receiving device 11. The output signals from the respective elements are integrated during a predetermined time, and 25-1, 25-2, 25-3 and 25-4 represent comparators connected respectively with the output terminals of the integration circuits 24-1, 24-2, 24-3 and 24-4. A preset reference voltage Vref is applied on the respective terminals of the comparators 25-1, 25-2, 25-3 and 25-4.

In the FIG. 3 embodiment, the detecting circuit 12 detects an uneven brightness distribution in the visual field, on the basis of a controlling signal from the detecting circuit, and the liquid crystal driving circuit 23 selectively makes the respective segments of the liquid crystal device 22 opaque. Thus, at the entrance end of the light guide 21, comparatively bright portions and comparatively dark portions will be produced by the opaque segments of the liquid crystal device 22 and since the light guide 21 is formed to substantially correspond at the entrance end and exit end, comparatively bright portions and comparatively dark portions also will be produced at the exit end of the light guide 21. Therefore, the light distribution characteristic on the object S to be observed by the above-mentioned illuminating system will be properly changed, and the brightness distribution in the visual field will be uniform.

The control of the brightness on the object S to be observed shall be further explained with reference to FIG. 3. In this embodiment, the light receiving device 11 is formed of four elements 11-1, 11-2, 11-3 and 11-4, each consisting, for example, of a photodiode or phototransistor. When a subject S is unevenly illuminated, (i.e. when the amount of light incident upon a particular element such as) 11-1 is large only the output from the integration circuit 24-1 will become higher than the reference voltage $V_{REF}$; therefore, only the comparator 25-1 will output a signal. By this signal, the power source circuit driving the segment 22-1 of the liquid crystal device 22 within the liquid crystal driving circuit 23 will be activated. Therefore, the light transmittance in the part of the liquid crystal device corresponding to the segment 22-1 will be reduced, and the brightness of the surface part of the object corresponding to that part will be reduced. Consequently, the brightness of the surface of the object S to be observed will be locally controlled and, as a whole, a uniform brightness will be maintained. In the FIG. 3 embodiment, the light receiving device 11 and the liquid crystal device 22 are divided into four elements; however, the number of the divided elements can be selected to be of a greater or lesser amount.

Figure 4:
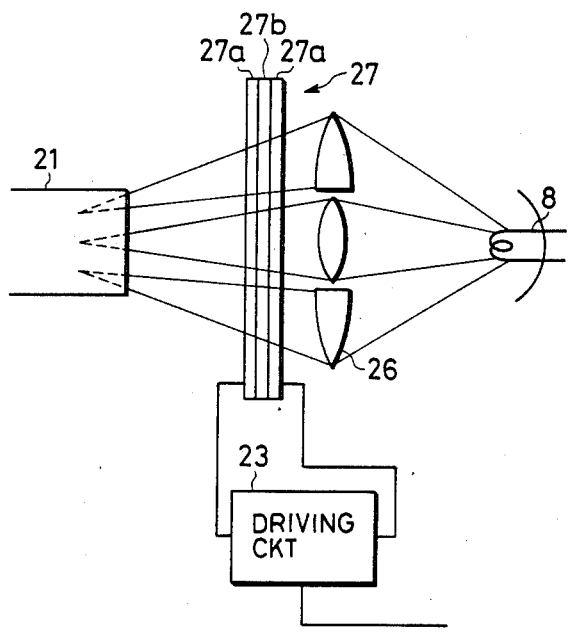
FIGS. 4, 5 and 7 are schematic views showing respectively different second, third and fourth embodiments of the illuminating optical system for endoscopes according to the present invention.

FIG. 4 shows a modification of the embodiment in FIG. 2. The reference numeral 26 represents a light collecting lens consisting of concentrically formed multi-focus circular lenses. The light source 8 and the entrance end of the light guide 21 are arranged so as to be in positions substantially conjugate with each other with respect to the light collecting lens 26. The reference numeral 27 represents a liquid crystal device arranged near the light collecting lens 26 between the light collecting lens 26 and the entrance end of the light guide 21 and having a liquid crystal 27b between two electrodes 27a as in the liquid crystal device 22 in FIG. 1. The other formations and operations are the same as in FIG. 1.

Figure 5:
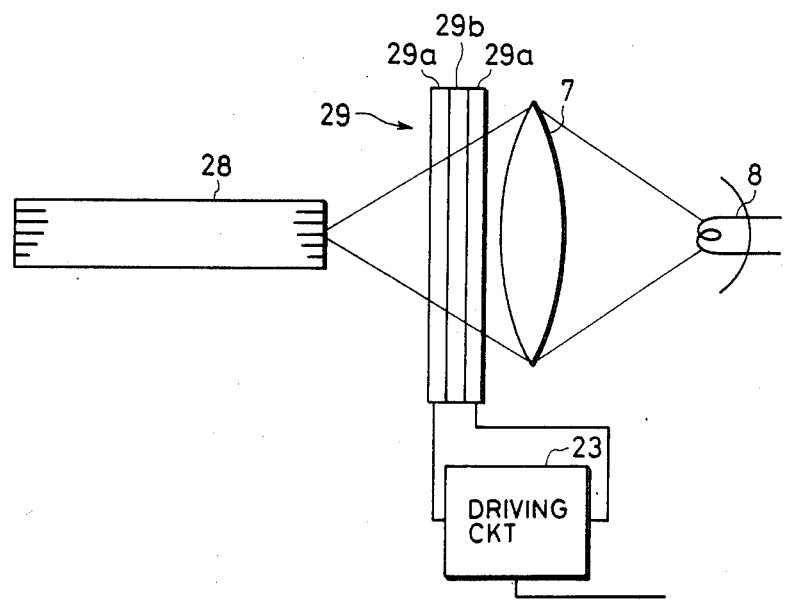
Figure 6:
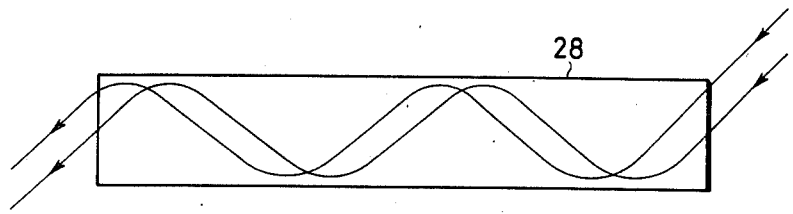
FIG. 6 is a view for explaining the action of graded index optical fibers.

FIG. 5 shows another embodiment of the present invention. The reference numeral 28 represents a light guide formed of a plurality of graded index optical fibers, and 29 represents a liquid crystal device arranged near the light collecting lens 7 between the light collecting lens 7 and the entrance end of the light guide 28 having a liquid crystal 29 between two electrodes 29a as in the liquid crystal device 22 in FIG. 1. The other formations are the same as in FIG. 1. According to this formation, since the entrance direction and exit direction of the liquid correspond to each other as shown in FIG. 6, when the driving circuit 23 selectively makes the respective segments of the liquid crystal device 29 opaque, the direction of the light incident upon the entrance end of the light guide 28 will be selected, thereby controlling the direction of the light coming out of the exit end of the light guide 28. The light distribution characteristic on the object S to be observed will be properly changed, and the brightness distribution in the visual field will be made uniform.

Figure 7:
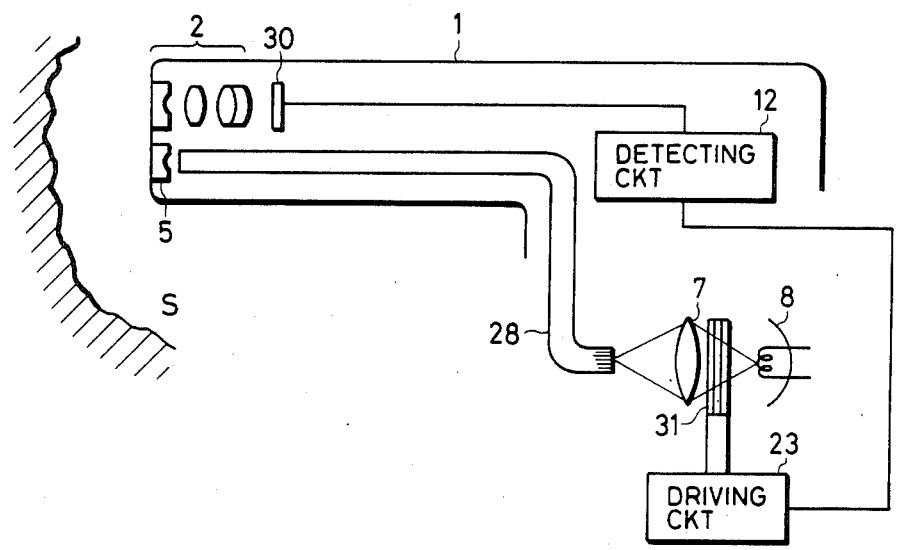

FIG. 7 shows a modification of the embodiment in FIG. 5 for an endoscope using a solid-state image sensor. The reference numeral 30 represents a solid-state image sensor arranged in the image forming position of the objective 2 and connected to an observing device not illustrated such that the brightness distribution in the visual field may be detected by the detecting circuit. The reference numeral 31 represents a liquid crystal device arranged between the liquid source 8 and light collecting lens 7 as in the liquid crystal device 22 in FIG. 2.

FIG. 8 shows a controlling circuit including the detecting circuit 12 and liquid crystal driving circuit 23 of FIG. 7. The reference numeral 32 represents a synchronizing signal generator; 33 represents a processing circuit; 35 represents a monitor TV, 36-1, 36-2, 36-3; . . . 36-n (n represents the number of sections on the solid-state image sensor) represent gate circuits; 37 represents a sampling pulse generating circuit which distributes pulses synchronized with clock pulses from the synchronizing signal generator in turn to the gate circuits 36-1, 36-2, . . . 36-n and to integration circuits 38-1, 38-2, 38-3, . . . 38-n; 39-1, 39-2, 39-3, . . . 39-n represent comparators connected respectively with the output terminals of the integration circuits 38-1, 38-2, 38-3, . . . 38-n; and 40 represents an integration circuit for integrating all of the outputs from the solid-state image sensor 30. The solid-state image sensor 30 is formed of many pixel elements; however, if the liquid crystal device is divided into fine segments corresponding to the respective pixel elements, no light variation may be detected. Therefore, as shown by hatchings in FIG. 8, the brightnesses in somewhat large sections 30-1, 30-2, . . made up of a predetermined number of pixel elements are detected for controlling the illumination. The segments 31-1, 31-2, . . . of the liquid crystal device 31 correspond respectively to the above-mentioned sections 30-1, 30-2, . . . of the solid-state image sensor 30. The reference voltage $V_{REF}$ applied on the respective terminals of the comparators 39-1, 39-2, 39-3, . . . 39-n may lie produced through a variable resistor on the basis of the output value from the integration circuit 40.

In the FIG. 8 embodiment, the solid-state image sensor 30 is driven with a predetermined clock pulse fed from the synchronizing signal generator, and an output signal is read out of each pixel element group. This signal is processed in the processing circuit 33 and is then processed in the same manner as an ordinary TV signal in the signal processing circuit 34 so that the image of the object S to be observed may be shown on the TV monitor 35. The output signal from the processing circuit 33 is simultaneously fed to the gate circuits 36-1, 36-2, 36-3, . . . 36-n. A pulse synchronized with the driving pulse of the solid-state image sensor 30 is distributed from the sample pulse generating circuit 37 to the gate circuits 36-1, 36-2, 36-3, . . . 36-n to open the gate circuits at predetermined timings such that, through the gate circuit 36-1, only the output from the pixel element group contained in the section 30-1 of the solid-state image sensor 30 may be fed to the integration circuit 38-1, through the gate circuit 36-2, only the output from the pixel element group contained in the section 30-2, and such that may be fed to the integration circuit 38-2 through the gate circuit 36-n, only the output from the pixel element group contained in the section 30-n may be fed to the integration circuit 38-n. Thus, the respective integration circuits 38-1, 38-2, 38-3, . . . 38-n integrate respectively the input signals, and the outputs from the respective integration circuits represent the totals in the respective sections 30-1, 30-2, . . . These respective outputs are fed respectively to the comparators 39-1, 39-2, . . . 39-n and are compared respectively with the reference voltage $V_{REF}$. The subsequent operations are the same as are explained with reference to FIG. 3. In the FIG. 8 embodiment, however, the reference voltage $V_{REF}$ is produced on the basis of the output value from the integration circuit 40; thus irrespective of the reflection factor of the object to be observed, the uneven illumination can be detected. That is to say, the lower the reflection factor of the observed object, the smaller is the $V_{REF}$, and the higher the reflection factor, the larger is the $V_{REF}$. Consequently, as the liquid crystal device 31 is arranged between the light collecting lens 7 and light source 8, a further uniform light distribution characteristic will be obtained on the object S to be observed. This embodiment is preferable particularly in the case of a solid-state image sensor of a narrow latitude.

In all the above embodiments, a dynamic scattering system requires no polarizing plate, loses no light amount, and is, therefore, desirable as a system for driving the liquid crystal device; however, the liquid crystal may be held between two polarizing plates so as to be operated by a twisted nematic system. Further, it is possible to use an electrochromic device instead of the liquid crystal device. Generally, the illuminating device for endoscopes tends to be bright in the center part of the visual field but dark in the peripheral part. In the formation of the device according to the present invention as described above, however, the illuminating light in the part brighter than a predetermined value is reduced to eliminate the uneven illumination. All the part to be observed need not be controlled but only the center part of the region to be illuminated need be controlled. In such a case, as in the embodiment in FIG. 2, the image receiving device may be made smaller. In the embodiment in FIG. 7, on the other hand, only the predetermined central region need be sampled with the pulse generator 37.

What is claimed is:

1. An illuminating optical system for endoscopes, comprising:
   a light guide with first and second ends, said light guide being comprised of a plurality of optical fibers arranged such that a light input at said first end of said light guide corresponds to a light output at said second end of said light guide;
   a light source disposed opposite said first end of said light guide;
   electro-optic means disposed between said light source and said first end of said light guide, said electro-optic means being divided into a plurality of segments, each of said segments corresponding to at least one of said optical fibers, said segments being controllable as to their light transmissivity;
   detecting means for detecting a brightness distribution of the light output at said second end of said light guide on an object to be observed; and
   driving means, responsive to said detecting means, for controlling said electro-optic means such that the quantity of light transmitted by a segment to said corresponding optical fibers is reduced when said detecting means detects that the quantity of light transmitted through said corresponding optical fibers is greater than a predetermined value.

2. An illuminating optical system according to claim 1 wherein said electro-optic means is a liquid crystal device.

3. An illuminating optical system according to claim 1 wherein said electro-optic means is an electrochromic device.

4. An illuminating optical system according to claim 1, further comprising a light collecting lens arranged between said light source and said first end of said light guide.

5. An illuminating optical system according to claim 4, wherein said light collecting lens comprises an annular lens arranged concentrically around a circular lens.

6. An illuminating optical system according to claim 1, wherein said detecting means comprises:
   a photoelectric converting means having a plurality of light receiving parts corresponding to said plurality of segments of said electro-optic means; and
   a judging means for determining whether an output of each of said light receiving parts of said photoelectric converting means exceeds said predetermined value, wherein said driving means is responsive to said judging means such that said segments of said electro-optic means corresponding to said light receiving parts of said photoelectric converting means whose output exceeds said predetermined value are controlled to reduce the quantity of light transmitted by said segments to said corresponding optical fibers.

7. An illuminating optical system according to claim 6, wherein said photoelectric converting means is a solid-state imaging device and said light receiving parts comprise a plurality of pixel elements of said solid-state imaging device.

8. An illuminating optical system for endoscopes, comprising:
   a light guide with first and second ends, said light guide being comprised of graded index optical fibers arranged such that a light input at said first end of said light guide corresponds to a light output at said second end of said light guide;
   a light source disposed opposite said first end of said light guide;
   electro-optic means disposed between said light source and said first end of said light guide, said electro-optic means being divided into a plurality of segments, each of said segments corresponding to at least one of said optical fibers, said segments being controllable as to their transmissivity;
   detecting means for detecting a brightness distribution of the light output at said second end of said light guide on an object to be observed; and
   driving means, responsive to said detecting means, for controlling said electro-optic means such that the quantity of light transmitted by a segment to said corresponding optical fibers is reduced when said detecting means detects that the quantity of light transmitted through said corresponding optical fibers is greater than a predetermined value.

9. An illuminating optical system according to claim 8, wherein said detecting means comprises:
   a photoelectric converting means having a plurality of light receiving parts corresponding to said plurality of segments of said electro-optic means; and
   a judging means for determining whether an output of each of said light receiving parts of said photoelectric converting means exceeds said predetermined value, wherein said driving means is responsive to said judging means such that said segments of said electro-optic means corresponding to said light receiving parts of said photoelectric converting means whose output exceeds said predetermined value are controlled to reduce the quantity of light transmitted by said segments to said corresponding optical fibers.

10. An illuminating optical system according to claim 9, wherein said photoelectric converting means is a solid-state imaging device and said light receiving parts comprise a plurality of pixel elements of said solid-state imaging device.

11. An illuminating optical system according to claim 8 wherein said electro-optic means is an electrochromic device.

12. An illuminating optical system according to claim 8, further comprising a light collecting lens arranged between said light source and said first end of said light guide.

13. An illuminating optical system according to claim 12, wherein said light collecting lens comprises an annular lens arranged concentrically around a circular lens.

14. An illuminating optical system according to claim 8, wherein said electro-optic means is a liquid crystal device.

* * * * *